United States Patent [19]

Eisenmann

[11] Patent Number: 5,304,494
[45] Date of Patent: Apr. 19, 1994

[54] METHOD OF ANALYZING HYDROCARBON OIL MIXTURES USING GEL-PERMEATION CHROMATOGRAPHY

[75] Inventor: Pierre Eisenmann, Paris, France

[73] Assignee: Schlumberger Technology Corporation, Houston, Tex.

[21] Appl. No.: 865,438

[22] Filed: Apr. 9, 1992

[30] Foreign Application Priority Data

Apr. 11, 1991 [FR] France .................. 91-04405

[51] Int. Cl.$^5$ ............ G01N 33/26; G01N 30/02; G01N 30/86
[52] U.S. Cl. .................... 436/60; 73/23.36; 73/61.52; 210/656; 364/497; 364/502; 436/30; 436/161
[58] Field of Search .................... 436/60, 30, 161; 422/70, 89; 210/656, 198.2; 73/61.57, 61/52, 23.22, 23.36; 364/497, 498, 499, 502, 422

[56] References Cited

U.S. PATENT DOCUMENTS

| | | | |
|---|---|---|---|
| 3,691,364 | 9/1972 | Baba et al. | 364/497 |
| 4,002,052 | 1/1977 | Bordet et al. | 73/23.36 |
| 4,163,475 | 8/1979 | Cha et al. | 166/251 |
| 4,174,629 | 11/1979 | Striegler | 73/61.52 |
| 4,353,242 | 10/1982 | Harris et al. | 73/23.36 |
| 4,365,303 | 12/1982 | Hannah et al. | 364/498 |
| 4,468,742 | 8/1984 | Jenden et al. | 364/497 |
| 4,620,284 | 10/1986 | Schnell et al. | 364/498 |
| 4,631,687 | 12/1986 | Kowalski et al. | 73/61.52 |
| 4,642,778 | 2/1987 | Hieftje et al. | 364/497 |
| 4,807,148 | 2/1989 | Lacey | 73/61.52 |
| 4,835,708 | 5/1989 | Frans | 364/497 |
| 4,941,101 | 7/1990 | Crilly | 73/61.57 |
| 5,046,846 | 9/1991 | Ray et al. | 364/498 |

OTHER PUBLICATIONS

Guieze, Paul and J. M. Williams "Determination of the Molar Mass of Petroleum Distillation Residues Using Gel Permeation Chromatography", J. Chromatography 312(1984) pp. 261-272.

*Primary Examiner*—James C. Housel
*Assistant Examiner*—Jan M. Ludlow

[57] ABSTRACT

A method of analyzing a mixture of hydrocarbon oils by using gel-permeation chromatography together with infrared detection. According to the method the signals from the infrared detector are combined to form fingerprints (M) which are characteristic of the samples being analyzed and which represent the molecular size distribution of the various hydrocarbon fractions in the samples. Then, the fingerprints are combined either to determine the concentration and the fingerprints of an unknown oil present in a mixture of two oils, or else the concentrations of n known oils in a mixture of the n oils.

8 Claims, 2 Drawing Sheets

METHOD OF ANALYZING HYDROCARBON OIL MIXTURES USING GEL-PERMEATION CHROMATOGRAPHY

BACKGROUND OF THE INVENTION

1. Field of the invention

The present invention relates to a method of analyzing hydrocarbon oil mixtures by gel-permeation chromatography.

More precisely, the present invention relates to a method whereby certain characteristics of a mixture of oils, such as the concentrations of the various different oils and/or the nature of one of the oils in the mixture can be determined.

The invention is particularly suitable for use in the oil industry, in particular in drilling and production fields.

2. Description of Prior Art

Petroleum oils are hydrocarbon oils constituted by mixtures of aliphatic hydrocarbons and aromatic hydrocarbons, and it is advantageous to be able to characterize and monitor such mixtures on site at exploration or production wells, and at sites where oil is transferred.

This type of monitoring can be performed by a spectrometer method using ultraviolet radiation as described in U.S. Pat. No. 4,609,821.

Gel-permeation is a technique that is widely used in the laboratory for analyzing petroleum oils or fractions. In this technique, the hydrocarbon oil is separated into fractions of different molecular masses, and these fractions may be identified at the outlet from the chromatography column by means of an appropriate detector, generally a diffractive index detector, an ultraviolet detector, or a flame ionization detector, as described in "Chromatography in petroleum analysis" Chromatographic Science Series, Vol. 11, pp. 287-294.

However, this technique is not easy to use for determining the "fingerprint" that enables a crude oil to be characterized, i.e. for establishing a curve showing the distribution of the constituents of the oil as a function of their molecular masses. Given that the detectors used have responses that vary depending on the substance analyzed, it is difficult to convert elution curves from a chromatography column into molecular mass distribution curves. As a result, this technique cannot be used for obtaining the molecular mass distribution of an oil sample without resorting to additional measurements as described at page 305 of the above-specified document.

The fingerprint of a crude oil is thus generally determined by gas chromatography making use of flame ionization detectors.

In "Journal of Chromatography", 312, 1984, pp. 261-272, P. Guieze and J. M. Williams describe the use of the gel-permeation technique for determining molecular mass in oil distillation residues by making use of three chromatography columns in series together with two detectors, namely an infrared detector and an ultraviolet detector for analyzing the fractions leaving the chromatography columns. In that case, a computer serves to convert the information coming from the two detectors into molecular masses.

That publication also mentions that the technique could be used for characterizing petroleum oils by means of the fingerprints provided by the two detectors, but until now, nobody has envisaged using gel-permeation for obtaining such fingerprints.

OBJECT OF THE INVENTION

An object of the present invention is to characterize hydrocarbon mixtures by using the gel-permeation technique.

A particular object of the present invention is to provide a method of analyzing mixtures of hydrocarbon oils by using the gel-permeation technique to form fingerprints that are characteristic of a mixture and fingerprints that are characteristic of certain constituents of the mixture so that it is possible from these fingerprints to determine either the concentration and the fingerprint of an unknown oil present in a mixture of two oils, or else the concentrations of n oils contained in a mixture of said n oils.

SUMMARY OF THE INVENTION

In a first implementation of the invention, a method of characterizing a hydrocarbon oil mixture including a known first hydrocarbon oil and an unknown second hydrocarbon oil, comprises the steps of:

separating the hydrocarbon oil mixture into hydrocarbon fractions of different molecular sizes by gel-permeation chromatography;

for each of said separated fractions, producing a signal that is representative of the number of C-H bonds in the fraction by infrared detection;

in response to said signals, determining a first fingerprint M which is a characteristic of the mixture and which represents the molecular size distribution of the various fractions;

separating the known first hydrocarbon oil by gel-permeation chromatography, producing signals representative of the number of C—H bonds by infrared detection of the separated fractions and determining a second fingerprint $H_1$ which is a characteristic of said known first oil under the same conditions as for the determination of said first fingerprint; and combining said first and second fingerprints to determine the concentration c of the known first oil in the mixture and possibly also the fingerprint $H_2$ of the unknown second oil.

For example, the concentration of known oil in the mixture may be determined by using a correlation method with the known oil of the mixture.

Mathematically, each fingerprint such as M, $H_1$, or $H_2$ (fingerprint of the unknown oil) represents a distribution function $F(\log_{10}(MM))$ where MM is the Molecular Mass, and physically it represents the abundance of C—H bonds as a function of the base-ten logarithm of the alkane equivalent molar mass.

The area under the fingerprint "F" is normalized to 1, which can be written as:

$$\int_a^b f(\log_{10}(MM)) d(\log_{10}(MM)) = 1$$

On the $\log_{10}(MM)$ scale, a and b represent the limit values between which the fingerprint extends.

The fingerprints M and $H_1$ are determined experimentally and an estimate is required of the fingerprint $H_2$ of the unknown oil and the mass concentration c of the first oil in the mixture.

These items are interrelated by the following equation:

$$M = (1-c) \cdot H_2 + c \cdot H_1$$

and the correlation method may be used to estimate the two unknowns in this equation: c and $H_2$.

In this method, for two distribution functions $f(x)$ and $g(x)$ defined over the interval $(a,b)$, the correlation between the two functions is defined by the following integral over the interval $(a,b)$:

$$Corr_{fg} = \int_a^b [f(x) - m_f(x)][g(x) - m_g(x)]dx$$

in which $m_f(x)$ and $m_g(x)$ represent the means of the functions f and g respectively over the interval $(a,b)$.

These are local means that depend on the X value $x_o$ where they are calculated:

$$m_f(x_o) = \frac{1}{2s} \int_{x_o - s}^{x_o + s} f(x)dx$$

$$m_g(x_o) = \frac{1}{2s} \int_{x_o - s}^{x_o + s} g(x)dx$$

where $x_o$ is such that $a \leq x_o \leq b$.

To calculate these local means, it is necessary to choose the parameter "s" that corresponds to the half-length of the sub-interval centered on $x_o$ and over which the integration is performed.

The concentration c of the known first oil is determined by correlating the distribution function represented by the fingerprint m with the distribution function represented by the fingerprint $H_1$ to obtain the term $CorrMH_1$, by correlating the distribution function represented by the fingerprint $H_1$ with itself to obtain the term $CorrH_1H_1$, and by evaluating c from the following equation:

$$c = \frac{CorrMH_1}{CorrH_1H_1}$$

Thus, starting from the basic equation of the mixture:

$$M = (1-c).H_2 + c.H_1$$

correlation is performed with the first oil giving:

$$CorrMH_1 = (1-c).CorrH_2H_1 = c.CorrH_1H_1$$

i.e.

$$c = \frac{CorrMH_1 - CorrH_2H_1}{CorrH_1H_1 - CorrH_2H_1}$$

Since the term $CorrH_2H_1$ cannot be evaluated (oil $H_2$ unknown), the following two approximations are introduced:

$$|CorrH_2H_1| << |CorrH_1H_1| \text{ and}$$

$$|CorrH_2H_1| << |CorrMH_1|$$

The following estimate $c_{est}$ thus deduced for the parameter c:

$$c_{est} = \frac{CorrMH_1}{CorrH_1H_1}$$

After this parameter $c_{est}$ has been estimated, the fingerprint $H_2$ characteristic of the unknown second oil can be determined from the fingerprints M and $H_1$ and from the parameter $c_{est}$.

This may be performed using the following equation:

$$M = (1-c).H_2 + c.H_1$$

on the basis of the contamination estimate $c_{est}$ as found above, thus leading to the following estimate $H_{2est}$ for the fingerprint of the second oil:

$$H_{2est} = \frac{1}{1 - c_{est}} \cdot M - \frac{c_{est}}{1 - c_{est}} \cdot H_1$$

in which M and $H_1$ are respectively the distribution functions represented by the fingerprints m and $H_1$.

Clearly this calculation requires $c_{est}$ to be different from 1, i.e. for M to be different from $H_1$. In the event that $c_{est}$ is equal to or nearly equal to 1, either $H_2 = 0$ in which case there is no second oil, or else the fingerprint of the second oil is identical or very close to that of the first oil and the method of the invention cannot be used for estimating c.

It is advantageous to observe that this estimate found for the second oil satisfies:

$$CorrH_{2est}H_1 = 0$$

(unless $M = H_1$, which is equivalent to $c_{est} = 1$).

From the definition of $H_{2est}$, the following can be deduced:

$$CorrH_{2est}H_1 = \frac{1}{1 - c_{est}} CorrMH_1 - \frac{c_{est}}{1 - c_{est}} CorrH_1H_1$$

$$(1 - c_{est}) \cdot CorrH_{2est}H_1 = CorrMH_1 - c_{est} \cdot CorrH_1H_1$$

The second member is zero by definition of $c_{est}$. I.e.:

$$CorrH_{2est}H_1 = 0 \text{ or } c_{est} = 1$$

The solution found for $H_{2est}$ thus corresponds to the solution which is the most highly decorrelated relative to the first oil.

Thus, the method of the invention makes it easy to determine the concentration of the known oil in the mixture and also to determine the fingerprint of the unknown oil.

In the oil industry, there are numerous applications for this method of analyzing two oils.

One of the most advantageous of these applications concerns detecting and identifying crude oil in oil-based drilling muds while drilling an exploration borehole.

According to another aspect of the invention, a method of detecting crude oil produced from a subsurface formation during drilling with drilling oil, comprises the steps of:

periodically separating the drilling oil into fractions of different molecular sizes by gel-permeation chromatography;

producing, for each separated fraction, a signal representative of the number of C—H bonds in the fraction by infrared detection;

in response to said signals, determining a fingerprint which is a characteristic of the drilling oil and which represents the molecular size distribution of the various separated fractions; and comparing the periodically determined fingerprints to detect the contamination of the drilling oil by the produced crude oil.

Preferably the method further comprises the step of identifying the fingerprint of the crude oil on the basis of the fingerprint of pure drilling oil and the fingerprint of drilling oil contaminated by the crude oil, using the method described above.

This method is most advantageous since obtaining the fingerprint of crude oil produced while drilling makes it possible to obtain information concerning the quality of the crude oil of the deposit very early.

The method may also be used for verifying that various samples taken from an open well do indeed have the same fingerprint, and to obtain information on the extent to which the stratum has been invaded by filtrate from the oil mud.

The method may also be used for testing downhole samples to observe how the composition of the petroleum varies as a function of the depth of the well.

In a second implementation of the invention, a method of determining the concentrations of a plurality of at least two known hydrocarbon oils in a mixture, comprises the steps of:

(a) forming a first fingerprint m which is a characteristic of the mixture by:

separating the mixture into hydrocarbon fractions of different molecular sizes by gel-permeation chromatography;

infrared detecting the separated fractions to provide for each separated fraction, a signal representative of the number of C—H bonds in the fraction; and in response to said signals, determining a fingerprint which represents the molecular size distribution of the separated fractions to provide said first fingerprint;

(b) forming a plurality of second fingerprints $H_1$—$H_n$ which are characteristics of the known hydrocarbon oils present in the mixture by gel-permeation chromatography with infrared detection of said known hydrocarbon oils under the same conditions as those for forming the first fingerprint; and (c) combining said first and second fingerprints M, $H_1$—$H_n$ to determine the concentrations of each of the known oils in the mixture.

This method may be used, for example, to monitor the composition of a mixture of oils obtained from a plurality of pipelines in a loading installation, in order to verify that the flow rate of each pipeline is properly adjusted and that the composition of the mixture does not vary over time.

From the fingerprint M and the fingerprints $H_1$—$H_n$, the concentrations $c_1, \ldots, c_{n-1}$, and $c_n$ of each of the n oils in the mixture may also be determined by a correlation method using M, $H_1, \ldots, H_{n-1}$, and $H_n$.

Taking the case of a mixture of three oils having respective mass concentrations $c_1, c_2, c_3$, it is possible to start from the basic mixture equation:

$$M = c_1.H_1 + c_2.H_2 + (1-c_1-c_2).H_3$$

in which the fingerprints M, $H_1$, $H_2$, and $H_3$ are known.

On the basis of this equation, four linear equations in $c_1$ and $c_2$ are obtained as follows by correlating successively with M, $H_1$, $H_2$, and $H_3$,:

$$CorrMM = c_1.CorrH_1M + c_2.CorrH_2M + (1-c_1-c_2).CorrH_3M$$

$$CorrMM_1 = c_1.CorrH_1H_1 + c_2.CorrH_2H_1 + (1-c_1-c_2).CorrH_3H_1$$

$$CorrMM_2 = c_1.CorrH_1H_2 + c_2.CorrH_2H_2 + (1-c_1-c_2).CorrH_3H_2$$

$$CorrMH_3 = c_1.CorrH_1H_3 + c_2.CorrH_2H_3 + (1-c_1-c_2).CorrH_3H_3$$

In theory, the equations relating M to $H_1$, $H_2$, and $H_3$ are accurate. The first equation is thus redundant since it is a linear combination of the other three. However, in practice, it is preferable to use the first equation to estimate possible error and to add information.

Thereafter, conventional techniques are used to solve a system of four equations in three unknowns or a system of three equations in three unknowns (if the first equation is omitted). For example, the least squares technique may be used.

For a mixture M of n oils $H_1, H_2, \ldots, H_n$ having respective mass concentrations $c_1, c_2, \ldots C_{n-1}$ and $c_n = 1 - (c_1 + c_2 + \ldots + c_{n-1})$, the procedure is the same with each distribution function M, $H_1, \ldots, H_{n-1}, H_n$ being correlated with the distribution functions M, $H_1, \ldots, H_{n-1}, H_n$ and by calculating $c_1, \ldots, c_{n-1}, c_n$ from the following linear equations:

$$CorrMJ = c_1 \cdot CorrH_1J + \ldots + c_{n-1} \cdot CorrH_{n-1}J + (1 - c_1 - \ldots - c_{n-1}) \cdot CorrH_nJ$$

in which the is represent M, $H, \ldots, H_{n-1}, H_n$.

As before, there remains a linear system of $(n+1)$ equations in n unknowns to be solved and this is done by using conventional techniques, e.g. the least squares technique.

BRIEF DESCRIPTION OF THE DRAWINGS

Other characteristics and advantages of the invention appear more clearly on reading the following description given by way of non-limiting example and made with reference to the accompanying drawings, in which:

FIG. 2 relates to the fingerprint M of a mixture of two oils;

FIG. 3 shows the fingerprint $H_1$ of the first oil in the mixture of FIG. 2;

FIG. 4 shows the fingerprint $H_2$ of the second oil in the mixture of FIG. 2 and as estimated by the method of the invention; and FIG. 5 shows the real fingerprint of the second oil in the mixture of FIG. 2.

DETAILED DESCRIPTION OF THE INVENTION

Figure 1:
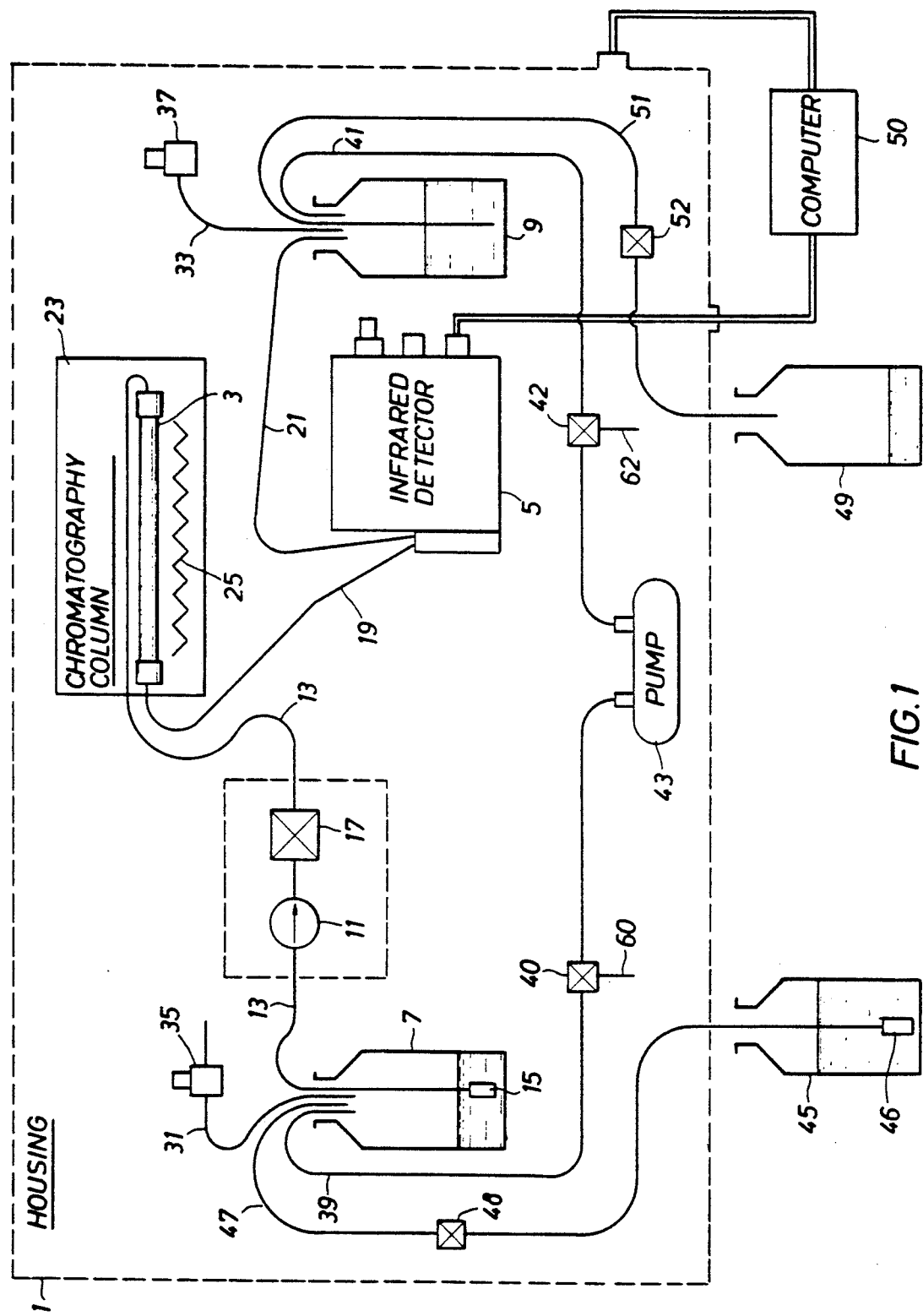
FIG. 1 is a block diagram of hydrocarbon oil analysis apparatus making use of gel-permeation chromatography.

FIG. 1 shows that the apparatus of the invention comprises a vibration-resistant sealed housing 1, having the following disposed therein: one or two gel-permeation chromatography columns 3; an infrared detector 5; a first flask 7 for fresh solvent; a second flask 9 for receiving used solvent; and a pump 11 for causing the fresh solvent from the first flask 7 to flow through the chromatography column 3 via a duct 13 having one of its ends immersed at the bottom of the flask 7 and including a filter 15 made of sintered material at said end.

An injector 17 may be used to inject the sample to be analyzed into the solvent that is caused to flow along the duct 13. After running along the column, the solvent containing the sample that has been fractionated by the shell is collected in a duct 19 and is then inserted into the infrared detector 5 after which it is exhausted via duct 21 into the second flask 9 for receiving used solvent.

The chromatography column 3 is disposed in a thermostatic enclosure 23 for maintaining the column 3 at a constant temperature that is slightly higher than ambient temperature. The heater means 25 of the thermostatic enclosure 23 are designed to enable temperatures of up to 100° C. to be obtained, thereby enabling the device to be used on sites in hot regions where outside temperatures may be about 50° C.

For the purpose of filling the first flask and emptying the second flask, each of the flasks is associated with various ducts suitable for enabling these operations to be performed by pneumatic means. To this end, the first flask 7 and the second flask 9 are associated via respective ducts 31 and 33 with valves 35 and 37 enabling these flasks to be put into communication with the atmosphere situated outside the housing during operation of the apparatus or to isolate them, thus sealing them completely during transport. The first flask 7 and the second flask 9 are also associated with respective ducts 39 and 41 provided with three-port valves 40 and 42 each connected firstly to a duct 60 or 62 leading to the atmosphere and secondly to a pump 43 suitable for sucking out the air present in the first flask 7 and for pumping air into the second flask 9. Finally, the first flask 7 may be connected to a source 45 of fresh solvent by a duct 47 fitted with a valve 48 and having one of its ends opening out into the top of the flask 7, and having its other end opening out into the bottom of the source 45 of fresh solvent via a filter 46.

Similarly, the second flask 9 is associated with an emptying receptacle 49 by a duct 51 provided with a valve 52 and opening out at one of its ends to the bottom of the second flask 9 and at its other end to the top of the emptying receptacle 49.

Thus, after switching the valve 42 so as to connect the circuit branch going from the pump 43 to the flask 9 to the atmosphere and then closing the valve 35, it is possible to fill the first flask 7 by suction by actuating the membrane pump 43. To empty the second flask 9, it suffices merely to actuate the membrane pump 43 similarly after closing the valve 37 and switching the valve 40 so as to put the other branch of the circuit going from the pump 43 to the flask 7 into communication with the atmosphere.

when both of the valves 40 and 42 are switched to their positions for communication with the atmosphere, it is possible to purge the membrane pump of residual vapors of carbon tetrachloride, which could damage the internal components of the pump.

The electrically controlled valves 35 and 37 may be controlled directly by switching on the apparatus and they are closed only when the membrane pump 43 is put into operation for solvent transfers.

To control various operations and to convert the signals output by the infrared detector 5 into a usable result, the apparatus may be associated with a portable computer 50 situated outside the sealed housing 1. This computer is designed to express its results in the form of fingerprints and to make use of them for determining the concentrations $c_1$ to $c_n$ of the various oils in a mixture and possibly also for determining the fingerprints of an unknown oil in the mixture.

In this apparatus, the various components may be constituted by conventional equipment as commonly used for gel-permeation chromatography.

To analyze a sample using this apparatus, the following procedure is used.

The valves 35 and 37 are opened to put the first and second flasks 7 and 9 into communication with the atmosphere, and the temperature of the column 3 is stabilized to the desired value by setting the thermostatically controlled enclosure 23 to a temperature which is about 5° C. higher than the outside temperature. Thereafter, the pump 11 is put into operation to cause solvent to flow through the column and the sample of oil to be analyzed is injected, the injected sample being previously diluted in solvent, e.g. to about 1/20th in carbon tetrachloride, with injection taking place via the injector 17 into the flow of solvent flowing along the duct 13.

As it flows along the column, the sample is fractionated into its various constituents, and these are detected at the outlet from the column by the infrared detector 5 which emits signals proportional to the number of CH bonds present. These signals are transformed by the computer 50 and then transcribed by the printer which is associated therewith in the form of a curve representing the molecular size distribution of the sample as split up by the gel-permeation chromatography column. The resulting fingerprints are then computer processed to calculate therefrom the unknown concentration values and/or the fingerprint of an unknown oil present in the oil mixture.

The following example shows how the method of the invention can be implemented to determine the extent to which an oil $H_1$ is contaminated by an oil $H_2$. This is an example for illustrating what the invention is capable of since the result is known a priori, however it is also estimated independently by using the method of the invention. This makes it possible to compare the result obtained by the invention with the real result.

To determine the degree of contamination, a sample of the mixture of the two oils (each oil representing 50% by weight in the mixture) together with a sample of each of the pure oils of the mixture is subjected to gel-permeation chromatography to obtain the fingerprint m of the mixture, the fingerprint $H_1$ of the pure first oil, and the real fingerprint $H_2$ of the pure second oil, all three fingerprints being obtained under the same conditions.

Figure 2:
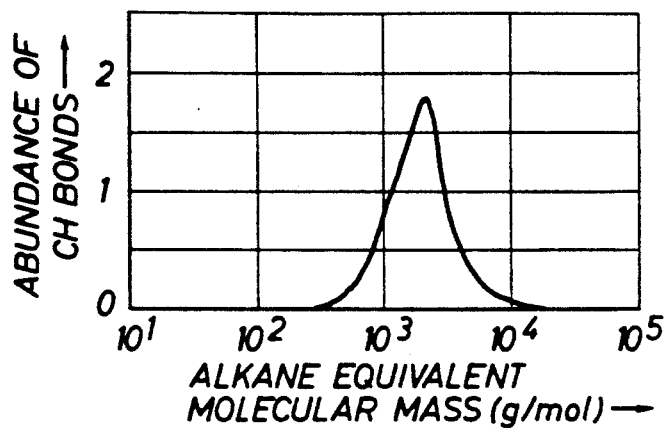
FIGS. 2 to 5 are hydrocarbon oil fingerprints obtained using the apparatus of FIG. 1.
Figure 3:
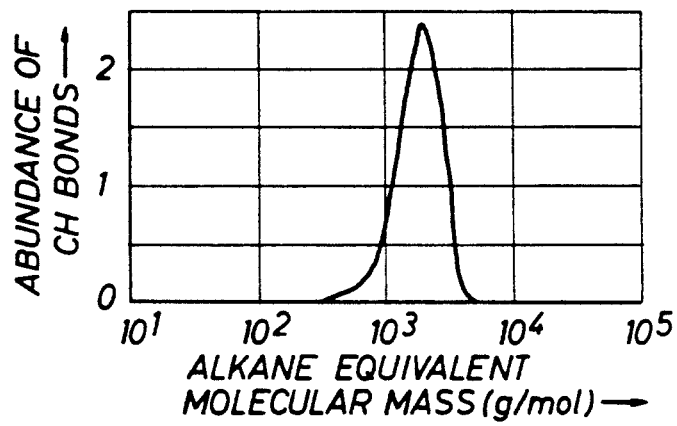
Figure 4:
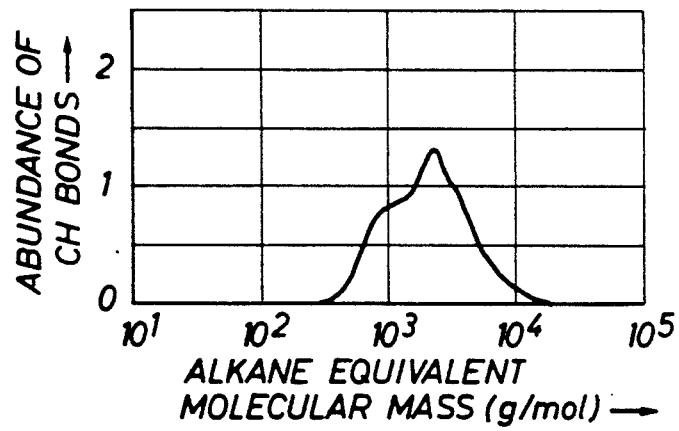

FIG. 2 shows the fingerprint M;
FIG. 3 shows the fingerprint $H_1$; and
FIG. 4 shows the estimated fingerprint $H_2$.

These figures are fingerprint curves representing the output signal from the infrared detector which is proportional to the number of C—H bonds in each fraction, i.e. to the molecular concentration of each fraction as a function of its molecular size, with the X-axis being calibrated by means of a normal alkane mixture so that the molecular sizes correspond to alkane equivalent molecular masses.

The fingerprints of FIGS. 2 and 3 are subsequently processed by the computer 50 in the manner described above to determine the amount of contamination c and to determine the fingerprint H₂ of the second oil.

In this way, it was found that the estimated amount of contamination c was 53%, which is very close to the real value of 50%.

Figure 5:
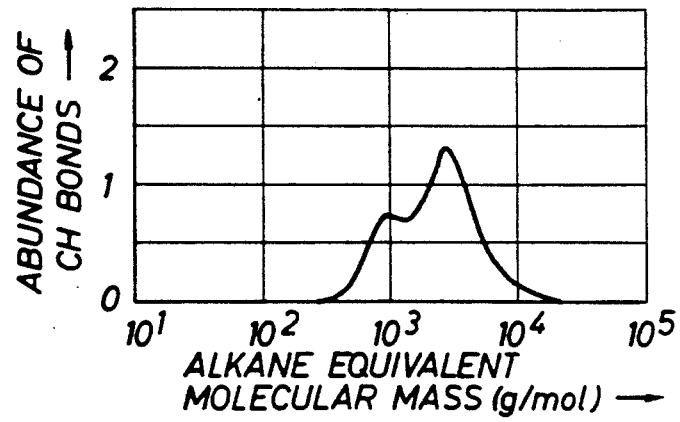

FIG. 5 shows the real fingerprint H₂ for the second oil. If FIG. 5 is compared with FIG. 4, it can be seen that the estimated fingerprint is practically identical to the real fingerprint of the second oil, thus showing clearly that the method of the invention is advantageous.

I claim:

1. A method of characterizing a hydrocarbon oil mixture comprising a known first hydrocarbon oil and an unknown second hydrocarbon oil having unknown composition and components, the method comprising the steps of:

separating the hydrocarbon oil mixture into first hydrocarbon fractions of different molecular sizes by gel-permeation chromatography;

for each of said first separated fractions, producing a signal that is representative of the number of C—H bonds in the fraction by infrared detection of said first separated fractions;

in response to said signals, determining a first fingerprint which is a characteristic of the mixture and which represents a molecular size distribution function of the first fractions;

separating the known first hydrocarbon oil into second hydrocarbon fractions by gel-permeation chromatography, producing signals representative of the number of C—H bonds by infrared detection of said second separated fractions and determining a second fingerprint which is a molecular size distribution function of said known first oil under the same conditions as for the determination of said first fingerprint; and correlating said first and second fingerprints to determine the concentration of the known first oil in the mixture.

2. A method according to claim 1, wherein said unknown second oil is oil produced from a deposit and wherein said known first oil is drilling oil.

3. A method according to claim 1, wherein said correlating step comprises:

correlating the distribution function represented by the first fingerprint with the distribution function represented by the second fingerprint to obtain a first correlation coefficient, CorrMH₁;

correlating the distribution function represented by the second fingerprint with itself to obtain a second correlation coefficient, CorrH₁H₁; and determining the concentration c of the known first oil in the mixture using the following equation:

$$c = \frac{CorrMH_1}{CorrH_1H_1}$$

in which M represents the distribution function represented by the first fingerprint, H₁ represents the distribution function represented by the second fingerprint and c is a number less than 1.

4. A method according to claim 3, wherein said correlation coefficients for two functions f and g are determined by the equation:

$$Corr_{fg} = \int_a^b [f(x) - m_f(x)][g(x) - m_g(x)]dx$$

in which a and b are limit values between which the fingerprint extends and (a,b) is the fingerprint interval, and $m_f(x)$ and $m_g(x)$ represent the means of the functions f and g respectively over the fingerprint interval and functions f and g are distribution functions Mo.

5. A method according to claim 3, further comprising the step correlating said first and second fingerprints and using said concentration of the known first oil to determine a third fingerprint which is a molecular size distribution function of the second oil.

6. A method according to claim 5, wherein said third fingerprint is determined from the equation:

$$H_2 = \frac{1}{1-c} \cdot M - \frac{c}{1-c} \cdot H_1$$

in which H₂ represents the molecular size distribution function represented by the third fingerprint, M represents the distribution function represented by the first fingerprint and H₁ represents the distribution function represented by the second fingerprint.

7. A method of detecting crude oil produced from a subsurface formation during drilling with drilling oil, wherein said drilling oil has been contaminated with said crude oil and wherein the composition and components of said crude oil are unknown, comprising the steps of:

separating said drilling oil into fractions of different molecular sizes by gel-permeation chromatography;

producing, for each separated fraction, a signal representative of the number of C—H bonds in the fraction by infrared detection;

in response to said signals, determining a first fingerprint which is a first molecular size distribution function of said drilling oil and which represents the molecular size distribution of the various separated fractions;

repeating said separating, producing and determining steps under the same conditions to determine a second fingerprint which is a second molecular size distribution of said drilling oil; and correlating said first and second fingerprints to detect contamination of said drilling oil by said produced crude oil.

8. A method according to claim 6, further comprising the step of identifying a fingerprint of said crude oil wherein the first fingerprint is a fingerprint of pure drilling oil and the second fingerprint is a fingerprint of drilling oil contaminated by the crude oil.

* * * * *